United States Patent
Smorenburg et al.

(10) Patent No.: US 10,362,665 B2
(45) Date of Patent: Jul. 23, 2019

(54) METHODS AND APPARATUS FOR OPTICAL METROLOGY

(71) Applicant: ASML Netherlands B.V., Veldhoven (NL)

(72) Inventors: Petrus Wilhelmus Smorenburg, Veldhoven (NL); Gerrit Jacobus Hendrik Brussaard, Boxtel (NL); Vadim Yevgenyevich Banine, Deurne (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/988,119

(22) Filed: May 24, 2018

(65) Prior Publication Data

US 2018/0368243 A1 Dec. 20, 2018

(30) Foreign Application Priority Data

Jun. 19, 2017 (EP) .................................... 17176638
Oct. 9, 2017 (EP) .................................... 17195462

(51) Int. Cl.
*H05G 2/00* (2006.01)
*G01N 21/956* (2006.01)
(Continued)

(52) U.S. Cl.
CPC ......... *H05G 2/008* (2013.01); *G01N 21/8806* (2013.01); *G01N 21/956* (2013.01);
(Continued)

(58) Field of Classification Search
USPC .......................................... 250/493.1, 504 R
See application file for complete search history.

(56) References Cited

U.S. PATENT DOCUMENTS

| 5,394,411 A * | 2/1995 | Milchberg ............... G21K 1/06 372/103 |
| 2003/0038255 A1* | 2/2003 | Bender ............... G03F 7/70016 250/504 R |

(Continued)

FOREIGN PATENT DOCUMENTS

WO    WO 2017/108404 A1    6/2017

OTHER PUBLICATIONS

Harada et al., "Development of standalone coherent EUV scatterometry microscope with high-harmonic-generation EUV source," Photomask and Next-Generation Lithography Mask Technology XIX, Proceedings of SPIE, vol. 8441, 2012; pp. I1-I10.

(Continued)

*Primary Examiner* — Kiet T Nguyen
(74) *Attorney, Agent, or Firm* — Sterne, Kessler, Goldstein & Fox P.L.L.C.

(57) ABSTRACT

Methods and apparatus for generation of radiation by high harmonic generation, HHG. The apparatus comprises: a chamber for holding a vacuum, the chamber comprising a radiation input, a radiation output and an interaction region at which, in use, a medium is present, the chamber being arranged such that, in use, when driving radiation propagates through the radiation input and is incident upon the medium, the medium emits radiation via HHG, the emitted radiation propagating through the radiation output; and at least one plasma generator at the radiation input and/or the radiation output for generating a plasma volume allowing the driving radiation and emitted radiation, respectively, to propagate through the plasma volume.

20 Claims, 8 Drawing Sheets

(51) Int. Cl.
G03F 7/20 (2006.01)
G01N 21/88 (2006.01)

(52) U.S. Cl.
CPC ........ *G03F 7/7065* (2013.01); *G03F 7/70616* (2013.01); *G03F 7/70625* (2013.01); *G03F 7/70633* (2013.01); *H05G 2/003* (2013.01); *G01N 2021/95676* (2013.01)

(56) References Cited

U.S. PATENT DOCUMENTS

2013/0329204 A1  12/2013  Pellemans et al.
2016/0282282 A1  9/2016  Quintanilha et al.
2017/0045823 A1  2/2017  Quintanilha

OTHER PUBLICATIONS

Libertun et al., "Design of fully spatially coherent extreme-ultraviolet light sources," American Institute of Physics, Applied Physics Letters, vol. 84, No. 19, May 10, 2004; pp. 3903-3905.

Hadrich et al., "Single-pass high harmonic generation at high repetition rate and photon flux," Journal of Physics B: Atomic, Molecular and Optical Physics, vol. 49, 2016; pp. 1-26.

Rothhardt et al., "Absorption-limited and phase-matched high harmonic generation in the tight focusing regime," New Journal of Physics, vol. 16, Mar. 19, 2014; pp. 1-15.

Heyl et al., "High-order harmonic generation with μJ laser pulses at high repetition rates," Journal of Physics B: Atomic, Molecular and Optical Physics, vol. 45, Mar. 16, 2012; pp. 1-9.

Hershcovitch A., "A plasma window for transmission of particle beams and radiation from vacuum to atmosphere for various applications," Physics of Plasmas, vol. 5, No. 5, May 1998; pp. 2130-2136.

Krasik et al., "Plasma window characterization," American Institute of Physics, Journal of Applied Physics, vol. 101, No. 053305, 2007; pp. 1-5.

De Beer et al., "Performance of a plasma window for a high pressure differentially pumped deuterium gas target for mono-energetic fast neutron production—Preliminary results," Nuclear Instruments and Methods in Physics Research B, vol. 170, 2000; pp. 259-265.

Raparia et al., "Plasma Window for SNS Target," BNL/SNS Technical Note No. 087, Collider-Accelerator Department Brookhaven National Laboratory, Feb. 12, 2001; 14 pages.

Glushko et al., "Self-Phase-Matching Mechanism for Efficient Harmonic Generation Processes in a Ring Pump Beam Geometry," The American Physical Society, Physical Review Letters, vol. 71, No. 2, Jul. 12, 1993; pp. 243-246.

Born et al., "Principles of Optics: Electromagnetic theory of propagation interference and diffraction of light," Seventh (Expanded) Edition, 1999; 31 pages.

Peatross et al., "High-order harmonic generation with an annular laser beam," Optical Society of America, Optics Letters, vol. 19, No. 13, Jul. 1, 1994; pp. 942-944.

Tang et al., "Evolution of low power laser affected by the plasma with Gaussian profile," Energy Science and Applied Technology—Fang (Ed.), 2016; pp. 321-324.

* cited by examiner

METHODS AND APPARATUS FOR OPTICAL METROLOGY

FIELD OF THE INVENTION

The invention relates to inspection tools and apparatus for optical metrology in relation to fabrication of logic and/or memory chips, e.g. by lithographic techniques. In particular, the invention may relate to inspection tools arranged to emit radiation by High Harmonic Generation (HHG) for optical metrology.

BACKGROUND

A lithographic apparatus is a machine that applies a desired pattern onto a target portion of the substrate. A lithographic apparatus can be used, for example, in the manufacture of logic and/or memory chips, termed integrated circuits (ICs) herein. In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. These target portions are commonly referred to as "fields".

In lithographic processes, it is desirable frequently to make measurements of the structures created, e.g., for process control and verification. This may be termed metrology. Various tools for making such measurements are known, including scanning electron microscopes (SEMs), which are often used to measure critical dimension (CD), and specialized tools to measure overlay, the accuracy of alignment of two layers in a device. Recently, various forms of optical tools or scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined.

At the same time, known inspection techniques employ radiation in the visible or ultraviolet waveband (e.g. greater than 200 nm). This limits the smallest features that can be measured, so that the technique can no longer measure directly the smallest features made in modern lithographic processes. To allow measurement of smaller structures, it has been proposed to use radiation of shorter wavelengths similar, for example, to the extreme ultraviolet (EUV) wavelengths used in EUV lithography. Such wavelengths may be in the range 1 to 100 nm, for example, or 1 to 125 nm. Part or all of this wavelength range may also be referred to as soft x-ray (SXR) wavelengths. Some authors may use SXR to refer to a narrower range of wavelengths, for example in the range 1-10 nm or 1-20 nm. For the purposes of the methods and apparatus disclosed herein, these terms SXR and EUV will be used without implying any hard distinction. Metrology using harder x-rays, for example in the range 0.1-1 nm is also contemplated.

Convenient sources of SXR radiation include HHG sources, in which infrared pump radiation from a laser is converted to shorter wavelength radiation by interaction with a gaseous medium. HHG sources are available for example from KMLabs, Boulder Colo., USA (http://www.kmlabs.com/).

Since the SXR photons of interest have a very short penetration depth in any medium, the gaseous medium may take the form of a gas jet located in a low-pressure (near vacuum) environment. The gas jet may be freely ejected from a nozzle, or confined within a waveguide structure that prolongs its interaction with the pump radiation.

Currently available SXR sources are very limited in output power. To enable inspection tools that both have high resolution and high throughput, there is therefore a need for high power SXR sources.

FIG. 1 shows a block schematic sketch of an apparatus 100 for use as an HHG source 100. The apparatus 100 comprises a pulsed high power infrared or optical laser 102, a chamber 104 comprising a radiation input 106 and a radiation output 108, and a vacuum optical system 110. The laser 102 emits driving radiation, which enters the chamber 104 through the radiation input 106 and is incident on a gas target 112 located at an interaction region 114 within the chamber 104. The gas target 112 comprises a small volume (typically several cubic mm) of a particular gas (e.g., a noble gas, nitrogen, oxygen or carbon dioxide). Other media, such as metallic plasmas (e.g. aluminium plasma) may be used.

Due to interaction of the driving radiation emitted by the laser 102 with the gas atoms of the gas target 112, the gas target 112 will convert part of the driving radiation into emitted radiation, which in this case comprises radiation at a plurality of wavelengths in the range from 1 nm to 100 nm (termed SXR herein). The emitted radiation is emitted in a direction collinear with the incident driving radiation.

The SXR beam passes through the radiation output 108 and is subsequently manipulated and directed to a wafer to be inspected by the vacuum optical system 110.

Because air (and in fact any gas) heavily absorbs SXR radiation, the volume between the gas target and the wafer to be inspected is evacuated or nearly evacuated. The driving radiation is directed into the chamber 104 through the radiation input 106, which is a viewport typically made of fused silica or a comparable material. Since the driving radiation and the emitted radiation (SXR beam) are collinear, the driving radiation typically needs to be blocked to prevent it passing through the radiation output 108 and entering the vacuum optical system 110. This is typically done by incorporating a filter into the radiation output 108, which is placed in the emitted beam path and that is opaque to the driving radiation (e.g. opaque to infrared or visible light) but at least partially transparent to the emitted radiation beam. The filter may be manufactured using zirconium.

In known HHG sources, a significant proportion of the emitted radiation beam is absorbed by the laser blocking filter used at the radiation output 108 to block the driving radiation. This leads to a loss of emitted radiation output power of typically 50%.

In addition, the viewport at the radiation input 106 through which the driving radiation enters the chamber 104 of the apparatus 100 has a number of disadvantages.

For example, part of the driving radiation is reflected and/or absorbed by the viewport. This may lead to a transmission loss of about 5-10% of the incident driving radiation. Given that the emitted radiation intensity of an HHG source is determined at least in part by the power of the driving radiation reaching the gas target 112, mitigation of this transmission loss would directly lead to 5-10% higher emitted radiation intensity.

Also, to reach high emitted radiation intensities, there is a tendency to tightly focus the driving radiation onto the gas target 112. In such tight-focus configurations, the gas target 112 will typically be placed relatively close to the viewport. Therefore the driving radiation will already be partially focused to relatively small beam cross-section when it enters the viewport, leading to high heat load on the viewport surface. Therefore the accessible range of tight-focusing configurations in an HHG source is currently limited by the material properties of the viewport and cooling system capacity. Mitigation of this heat load problem would extend the accessible range of focusing geometries.

In addition, driving radiation propagating through the viewport is prone to beam degradation due to material defects and surface imperfections of the viewport. Beam degradation leads to reduced ability to focus of the driving radiation beam, which reduces the range of intensities that can be reached in the focal spot at the gas target 112. Since the HHG mechanism and thereby the properties of the emitted radiation beam sensitively depend on the driving radiation intensity distribution, beam degradation due to the viewport results in reduced control of the emitted radiation intensity and beam properties.

SUMMARY

The invention aims to improve the output power of an apparatus for generation of radiation by high harmonic generation.

According to the invention in an aspect, there is provided an apparatus for generation of radiation by high harmonic generation, HHG, the apparatus comprising: a chamber for holding a vacuum, the chamber comprising a radiation input, a radiation output and an interaction region at which, in use, a medium is present, the chamber being arranged such that, in use, when driving radiation propagates through the radiation input and is incident upon the medium, the medium emits radiation via HHG, the emitted radiation propagating through the radiation output; and at least one plasma generator at the radiation input and/or the radiation output for generating a plasma volume allowing the driving radiation and emitted radiation, respectively, to propagate through the plasma volume.

Optionally, the at least one plasma generator is an output plasma generator at the radiation output and is configured to generate an output plasma volume for filtering the driving radiation such that less driving radiation exits the output plasma volume than enters the output plasma volume.

Optionally, the output plasma generator is configured to generate the output plasma volume for altering one or more properties of the driving radiation to a greater degree than the same one or more properties of the emitted radiation.

Optionally, the one or more properties comprise a spatial profile of the driving and emitted radiation.

Optionally, the output plasma generator is configured to generate the output plasma volume for transforming the driving radiation from a substantially lowest order Gaussian spatial profile to a substantially annular spatial profile.

Optionally, the chamber further comprises an aperture at the radiation output sized to block at least part of the driving radiation and to allow the emitted radiation to pass through.

Optionally, at least part of the emitted radiation is substantially spatially confined within the annular spatial profile of the driving radiation.

Optionally, the output plasma generator is configured to generate the output plasma volume for deflecting the driving radiation radially away from an output optical axis of the apparatus.

Optionally, the output plasma generator comprises a cylindrical channel, and is configured to generate the output plasma volume with a density of free electrons decreasing radially from an output optical axis through the cylindrical channel.

Optionally, the decrease in the density of free electrons in the output plasma volume has a parabolic function.

Optionally, the output plasma generator is configured to generate the output plasma volume having a length, L, in a range determined by $$L > \sqrt{-\frac{2R^2 n_{cr} \ln F_1}{\eta n_a}}$$

and $$L < -\frac{\ln F_2}{\sigma(1-\eta)n_a}$$

where $\eta$ is a degree of ionization within the plasma, $n_a$ is an ionized atom density on the output optical axis, R is the root mean square width of the Gaussian function, $n_{cr}$ is the critical electron density, $\sigma$ is a cross section for absorption of the emitted radiation by atoms, ions and/or molecules in the output plasma volume, $F_1$ is an attenuation factor of the driving radiation and $F_2$ is an attenuation factor of the emitted radiation.

Optionally, the output plasma generator is configured to generate the output plasma volume as an arc plasma and optionally a cascaded arc plasma comprising a noble gas or hydrogen.

Optionally, the output plasma generator is configured to generate the output plasma volume using laser ionization and optionally having a degree of ionization of greater than 50%.

Optionally, the at least one plasma generator comprises an input plasma generator at the radiation input and is configured to generate an input plasma volume for holding the vacuum in the chamber.

Optionally, the input plasma generator is configured to generate the input plasma volume using one of the noble gases.

Optionally, the noble gas is argon.

Optionally, the input plasma generator is configured to generate the input plasma volume for transforming the driving radiation from a substantially lowest order Gaussian spatial profile to a substantially annular spatial profile.

Optionally, the input plasma generator is configured to generate the input plasma volume for focussing the driving radiation at the interaction region.

Optionally, the input plasma generator comprises a cylindrical channel, and is configured to generate the input plasma volume having a density of free electrons decreasing radially from an input optical axis through the cylindrical channel.

Optionally, a length of the input plasma volume is in a range from 30 mm to 100 mm and/or wherein a diameter of the input plasma volume is in a range from 3 mm to 55 mm.

Optionally, the driving radiation has a wavelength in a range from 0.8 μm to 1.2 μm and/or wherein the emitted radiation comprises radiation at multiple wavelengths in a range from 1 nm to 100 nm.

Optionally, the interaction region comprises a chamber configured to hold a gas.

Optionally, the gas is one of a noble gas and air.

According to the invention in an aspect, there is provided an inspection apparatus comprising an apparatus described herein, and further comprising a substrate table for holding a substrate and optics for directing the emitted radiation onto the substrate.

Optionally, the inspection apparatus is a metrology apparatus.

According to the invention in an aspect, there is provided a method for generating radiation by high harmonic generation, HHG, using an apparatus comprising: a chamber comprising a radiation input, a radiation output and an interaction region at which, in use, a medium is present; and at least one plasma generator at the radiation input and/or the radiation output, the method comprising: generating, by the at least one plasma generator, a plasma volume at the radiation input and/or a plasma volume at the radiation output; and propagating driving radiation through the radiation input such that the driving radiation is incident upon the medium, causing the medium to emit radiation via HHG, the emitted radiation propagating through the radiation output, wherein the plasma volume at the radiation input allows the driving radiation to propagate through, and the plasma volume at the radiation output allows the emitted radiation to propagate through.

Optionally, the plasma volume comprises an output plasma volume at the radiation output that filters the driving radiation such that less driving radiation exits the output plasma volume than enters the output plasma volume.

Optionally, the output plasma volume alters one or more properties of the driving radiation to a greater degree than the same one or more properties of the emitted radiation.

Optionally, the one or more properties comprise a spatial profile of the driving and emitted radiation.

Optionally, the output plasma volume transforms the driving radiation from a substantially lowest order Gaussian spatial profile to a substantially annular spatial profile.

Optionally, the chamber further comprises an aperture at the radiation output, which blocks at least part of the driving radiation and allows the emitted radiation to pass through.

Optionally, at least part of the emitted radiation is substantially spatially confined within the annular spatial profile of the driving radiation.

Optionally, the output plasma volume deflects the driving radiation radially away from an output optical axis of the apparatus.

Optionally, the output plasma generator comprises a cylindrical channel, and the output plasma volume has a density of free electrons decreasing radially from an output optical axis through the cylindrical channel.

Optionally, the decrease in the density of free electrons in the output plasma volume has a parabolic function.

Optionally, the output plasma volume has a length, L, in a range determined by $$L > \sqrt{-\frac{2R^2 n_{cr} \ln F_1}{\eta n_a}}$$

and $$L < -\frac{\ln F_2}{\sigma(1-\eta)n_a}$$

where $\eta$ is a degree of ionization within the plasma, $n_a$ is an ionized atom density on the output optical axis, R is the root mean square width of the Gaussian function, $n_{cr}$ is the critical electron density, $\sigma$ is a cross section for absorption of the emitted radiation by atoms, ions and/or molecules in the output plasma volume, $F_1$ is an attenuation factor of the driving radiation and $F_2$ is an attenuation factor of the emitted radiation.

Optionally, the output plasma volume as an arc plasma and optionally a cascaded arc plasma comprising a noble gas or hydrogen.

Optionally, the output plasma generator generates the output plasma volume using laser ionization and optionally the output plasma volume has a degree of ionization of greater than 50%.

Optionally, the plasma volume comprises an input plasma volume at the radiation input that holds the vacuum in the chamber.

Optionally, the input plasma generator generates the input plasma volume using one of the noble gases.

Optionally, the noble gas is argon.

Optionally, the input plasma volume transforms the driving radiation from a substantially lowest order Gaussian spatial profile to a substantially annular spatial profile.

Optionally, the input plasma volume focusses the driving radiation at the interaction region.

Optionally, the input plasma generator comprises a cylindrical channel, and the input plasma volume has a density of free electrons decreasing radially from an input optical axis through the cylindrical channel.

Optionally, a length of the input plasma volume is in a range from 30 mm to 100 mm and/or a diameter of the input plasma volume is in a range from 3 mm to 55 mm.

Optionally, the driving radiation has a wavelength in a range from 0.8 µm to 1.2 µm and/or the emitted radiation comprises radiation at multiple wavelengths in a range from 1 nm to 100 nm.

Optionally, the interaction region comprises a chamber configured to hold a gas.

Optionally, the gas is one of a noble gas and air.

According to the invention in an aspect, there is provided a computer program comprising instructions which, when executed on at least one processor, cause the at least one processor to control an apparatus to carry out a method according to any described herein.

According to the invention in an aspect, there is provided a carrier containing the computer program mentioned above, wherein the carrier is one of an electronic signal, optical signal, radio signal, or non-transitory computer readable storage medium.

BRIEF DESCRIPTION OF THE DRAWINGS

Embodiments of the invention will now be described, by way of example only, with reference to the accompanying schematic drawings, in which.

DETAILED DESCRIPTION

Generally, disclosed herein are methods and apparatus in which a plasma volume is generated at one or both of the radiation input and the radiation output of a chamber of an apparatus for use as an HHG radiation source.

When placed at the radiation output, a plasma volume (output plasma volume) may be configured to allow emitted radiation (e.g. an SXR beam) to propagate through and may be further configured to reduce the power of any driving radiation (e.g. laser light) propagating through. In exemplary arrangements, the output plasma volume may be configured to filter the driving radiation such that less driving radiation exits the output plasma volume than enters the output plasma volume. This may be done, for example, by attenuation and/or deflection.

When placed at the input, a plasma volume (input plasma volume) is configured to allow driving radiation to pass through and may be configured to provide a barrier between two volumes of different pressures. For example, the input plasma volume may provide a barrier between the vacuum or near vacuum of the chamber and atmosphere external to the chamber.

Before describing embodiments of the invention in detail, it is instructive to present an example environment in which embodiments of the present invention may be implemented.

Figure 2A:
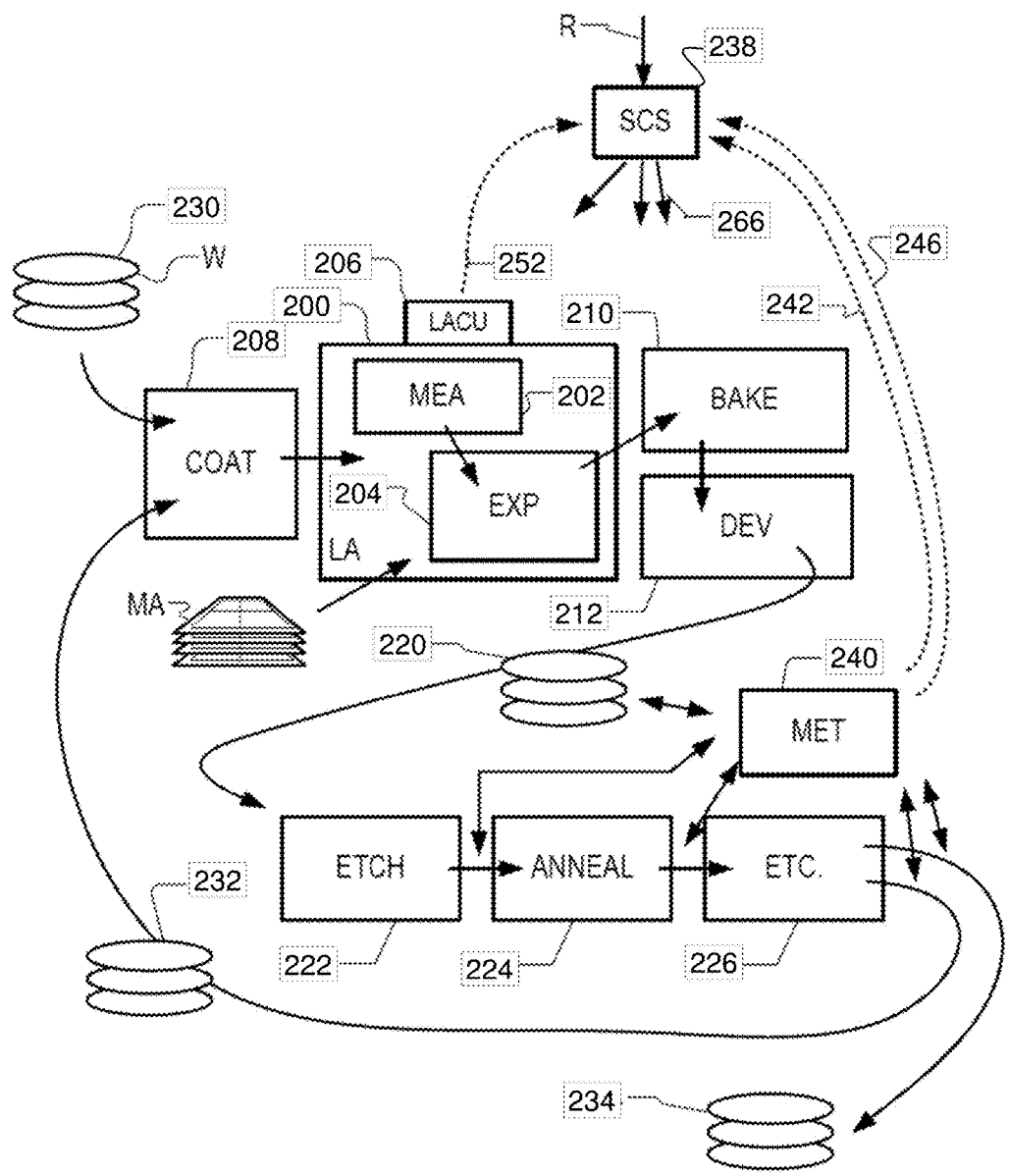
FIG. 2a is a schematic representation of a lithographic apparatus as part of an industrial facility.
Figure 2B:
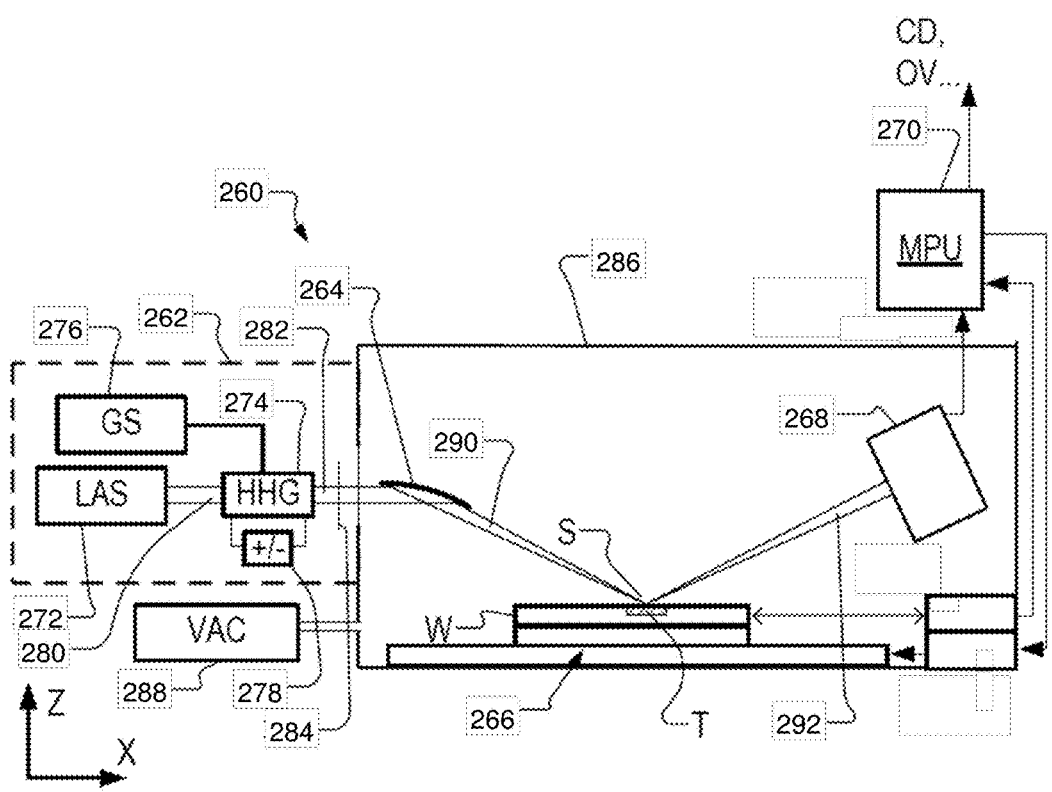
FIG. 2b is a schematic representation of an inspection apparatus.

FIG. 2 shows a schematic representation of a lithographic apparatus 200 (LA) as part of an industrial facility implementing a high-volume, lithographic manufacturing process. In the example of FIG. 2, the manufacturing process is adapted for the manufacture of semiconductor products (e.g. ICs) on substrates such as semiconductor wafers. The skilled person will appreciate that a wide variety of products can be manufactured by processing different types of substrates in variants of this process. The production of semiconductor products is used purely as an example.

The lithographic apparatus (or "litho tool" for short) 200 comprises a measurement station 202 (MEA) and an exposure station 204 (EXP). A control unit 206 (LACU) is also shown. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The LACU 206 controls all the movements and measurements of various actuators and sensors, causing the apparatus to receive substrates W and reticles MA and to implement the patterning operations. The LACU 206 also includes signal processing and data processing capacity to implement desired calculations relevant to the operation of the apparatus. In practice, the LACU 206 may be realized as a system of many sub-units, each handling the real-time data acquisition, processing and control of a subsystem or component within the apparatus.

Before the pattern is applied to a substrate at the exposure station 204, the substrate is processed at the measurement station 202 so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy.

The lithographic apparatus 200 may be of a so-called dual stage type which has two substrate tables, each with a positioning system controlled by the control unit LACU. While one substrate on one substrate table is being exposed at the exposure station 204, another substrate can be loaded onto the other substrate table at the measurement station 202 so that various preparatory steps may be carried out. The measurement of alignment marks is therefore very time-consuming and the provision of two substrate tables enables a substantial increase in the throughput of the apparatus. If the position sensor is not capable of measuring the position of the substrate table while it is at the measurement station as well as at the exposure station, a second position sensor may be provided to enable the positions of the substrate table to be tracked at both stations.

When lithographic apparatus 200 is of a so-called dual stage type which has two substrate tables, the exposure station 204 and the measurement station 202 may be distinct locations between which the substrate tables can be exchanged. This is only one possible arrangement, however, and the measurement station 202 and exposure station 204 need not be so distinct. For example, it is known to have a single substrate table, to which a measurement stage 202 is temporarily coupled during the pre-exposure measuring phase. The methods and apparatus disclosed herein are not limited to any of the above types of system.

Within the production facility, lithography apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatus, substrate handling systems take care of supporting the substrates and transferring them from one piece of apparatus to the next. These substrate handling systems, which are often collectively referred to as the "track", are under the control of a track control unit which is itself controlled by a supervisory control system 238 (SCS), which also controls the lithographic apparatus 200 via the LACU 206. Thus, the different apparatus can be operated to maximize throughput and processing efficiency. The SCS 238 receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, and 226. A wide range of processing steps is implemented by various apparatuses in a typical manufacturing facility. For the sake of example, apparatus 222 in this embodiment is an etching station and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

The manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatus 222, 224, 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system 240 (MET) which receives some or all of the substrates W that have been processed in the litho cell. Metrology results 242, 246 are provided directly or indirectly to the SCS 238. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

The metrology apparatus 240 is provided for making measurements of parameters of the products at desired stages in the manufacturing process. A common example of a metrology apparatus 240 in a modern lithographic production facility is a scatterometer, for example an angle-resolved scatterometer or a spectroscopic scatterometer, and it may be applied to measure properties of the developed substrates at 220 prior to etching in the apparatus 222.

Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. The metrology results 242, 246 from the apparatus 240 can be used to maintain accurate performance of the patterning operations in the litho cluster, by the SCS 238 and/or the LACU 206 making small adjustments over time, thereby minimizing the risk of products being made out-of-specification, and requiring re-work. Of course, the metrology apparatus 240 and/or other metrology apparatuses (not shown) can be applied to measure properties of the processed substrates 232, 234, and incoming substrates 230.

The metrology apparatus 240 may if desired implement a hybrid metrology system. A common example of a metrology apparatus in a modern lithographic production facility is a scatterometer, for example an angle-resolved scatterometer or a spectroscopic scatterometer, and it may be applied to measure properties of the developed substrates at 220 prior to etching in the apparatus 222.

Each generation of lithographic manufacturing technology (commonly referred to as a technology "node") has tighter specifications for performance parameters such as CD. One of the main challenges in metrology is that the size of features within the products become smaller and smaller and this smaller feature size should be reflected also in the design of metrology targets. Accordingly, the metrology apparatus 240 may include an inspection apparatus designed to operate with radiation at wavelengths shorter than conventional visible or UV wavelengths. As particular examples, radiation with wavelengths in the ranges 1 nm to 10 nm, 5 nm to 50 nm and 1 nm to 100 nm may be used. More generally, radiation wavelengths may be described as SXR or EUV wavelengths.

Rather than rely for all purposes on a single inspection apparatus, a variety of inspection apparatuses may be used in practice. A hybrid metrology system may include scatterometers working at different wavelengths, and additional types of inspection apparatus, so that multiple types of measurement can be performed within the hybrid metrology system to obtain a better overall measurement of a parameter or parameters of interest on a given target structure.

Each of the inspection apparatuses within a hybrid metrology system can have a particular illumination system for radiation of a particular characteristic. For the purposes of the methods and apparatus disclosed herein, it is assumed that the metrology apparatus 240 is an inspection apparatus using soft x-ray (SXR) or extreme ultraviolet (EUV) radiation in a waveband shorter than 100 nm. For the purposes of the methods and apparatus disclosed herein, the terms SXR and EUV will be used without implying any hard distinction. This inspection apparatus using EUV or SXR radiation can be applied as one of the inspection apparatuses in a hybrid metrology system, but can also be applied independently, if desired.

FIG. 2a illustrates a schematic physical arrangement of an inspection apparatus 260 comprising a spectroscopic scatterometer using EUV/SXR radiation in grazing incidence, purely by way of example. An alternative form of inspection apparatus might be provided in the form of an angle-resolved scatterometer, which uses radiation in normal or near-normal incidence similar to the conventional scatterometers operating at longer wavelengths. Inspection apparatus 260 comprises a radiation source 262, illumination system 264, substrate support 266, detection system 268 and metrology processing unit (MPU) 270. Source 262 in this example comprises a generator of EUV or soft x-ray radiation based on HHG techniques. The main components of the radiation source 262 are a drive laser 272 and an HHG gas cell 274. A gas supply 276 supplies suitable gas to the gas cell 274, where it is optionally ionized by an electric source 278. The drive laser 272 may be for example a fiber-based laser with an optical amplifier, producing pulses of infrared radiation that may last for example less than 1 ns per pulse, with a pulse repetition rate up to several megahertz, as required. The wavelength of the infrared radiation may be for example in the region of 1 μm. The laser pulses are delivered as a first radiation beam 280 to the HHG gas cell 274, where in the gas a portion of the radiation is converted to higher frequencies than the first radiation into a beam 282 including coherent second radiation of the desired wavelength or wavelengths.

The second radiation may contain multiple wavelengths. If the radiation were monochromatic, then measurement calculations (for example reconstruction) may be simplified, but it is easier with HHG to produce radiation with several wavelengths. The volume of gas within the gas cell 274 defines an HHG space, although the space need not be completely enclosed and a flow of gas may be used instead of a static volume. The gas may be for example a noble gas such as neon (Ne) or argon (Ar). $N_2$, $O_2$, He, Ar, Kr, Xe gases can all be considered. These may even be selectable options within the same apparatus. Different wavelengths will, for example, provide different levels of contrast when imaging structure of different materials. For inspection of metal structures or silicon structures, for example, different wavelengths may be selected to those used for imaging features of (carbon-based) resist, or for detecting contamination of such different materials. Optionally, one or more filtering devices 284 may be provided. For example a filter such as a thin membrane of Aluminum (Al) may serve to cut the fundamental IR radiation from passing further into the inspection apparatus. A grating (not shown) may be provided to select one or more specific harmonic wavelengths from among those generated in the gas cell. Some or all of the beam path may be contained within a vacuum environment, bearing in mind that SXR radiation is absorbed when traveling in air. The various components of radiation source 262 and illumination system 264 can be adjustable to implement different metrology 'recipes' within the same apparatus. For example different wavelengths and/or polarization can be made selectable.

From the radiation source 262, the beam 282 enters an inspection chamber 286 where the substrate W including a structure of interest is held for inspection by substrate support 266. The structure of interest is labeled T. The atmosphere within inspection chamber 286 is maintained near vacuum by vacuum pump 288, so that EUV radiation can pass with-out undue attenuation through the atmosphere. The Illumination system 264 has the function of focusing the radiation into a focused beam 290, and may comprise for example a two-dimensionally curved mirror, or a series of one-dimensionally curved mirrors, as described in international application number PCT/EP2016/080058. The focusing is performed to achieve a round or elliptical spot S with a diameter that is optionally under 10 μm, when projected onto the structure of interest. Substrate support 266 comprises for example an X-Y translation stage and a rotation stage, by which any part of the substrate W can be brought to the focal point of beam to in a desired orientation. Thus the radiation spot S is formed on the structure of interest.

Reflected radiation 292 is captured by detector 268 and a spectrum is provided to processor 270 for use in calculating a property of the target structure T. The source 262 illumination system 264 and detection system 268 thus form part of an inspection apparatus 260. This inspection apparatus 260 may comprise an SXR spectroscopic reflectometer of the kind described in US2016282282A1. Tilting of the substrate W in one or more dimensions may also be provided.

As mentioned an alternative form of inspection apparatus uses SXR radiation at normal incidence or near-normal incidence, for example to perform diffraction-based measurements of asymmetry. Both types of inspection apparatus could be provided in a hybrid metrology system. Performance parameters to be measured can include overlay (OVL), critical dimension (CD), coherent diffraction imaging (CDI) and at-resolution overlay (ARO) metrology. The radiation emitted from the HHG chamber 274 may for example have wavelengths less than 100 nm, for example having wavelengths in the range 5-30 nm, or optionally in a range from 10-20 nm. The radiation may be narrowband or broadband in character. The radiation may also be a number of narrowband emissions within a relatively wide band.

Like the optical scatterometer used in today's production facilities, the inspection apparatus 260 can be used to measure structures within the resist material treated within the litho cell (After Develop Inspection or ADI), and/or to measure structures after they have been formed in harder material (After Etch Inspection or AEI). For example, substrates may be inspected using a metrology apparatus after they have been processed by the developing apparatus 212, etching apparatus 222, annealing apparatus 224 and/or other apparatus 226.

Figure 3:
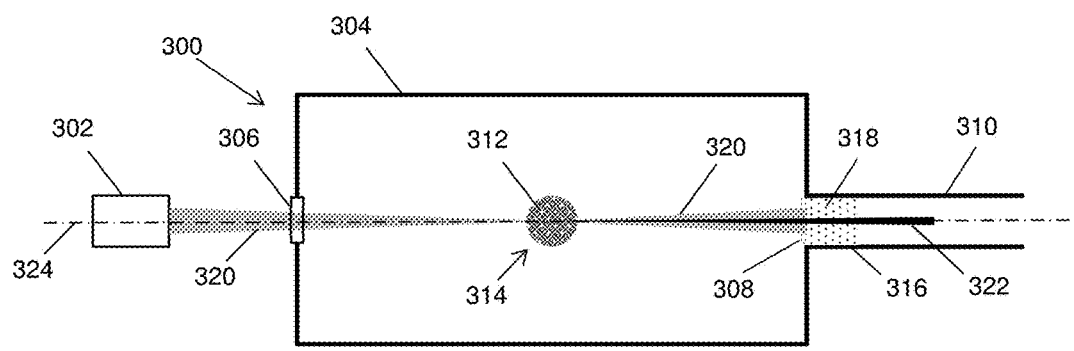
FIG. 3 is a schematic cross-sectional view of an apparatus for use as an HHG radiation source.

FIG. 3 shows a schematic representation of an apparatus 300 for producing radiation (e.g. in a wavelength range from 1 nm-100 nm) by HHG, which may be included in an inspection apparatus, such as the metrology apparatus 240. The apparatus 300 includes a number of features that are the same or similar to features shown in FIG. 1 and such features may use the same reference numeral, prefixed with a "3" instead of a "1". In general, features of FIG. 3 are discussed insofar as they differ from those of FIG. 1.

The apparatus 300 of FIG. 3 includes an output plasma generator 316 at the radiation output 308 of the chamber 304. The output plasma generator 316 is configured to generate an output plasma volume 318 that allows radiation emitted from a medium 312 to propagate through. Therefore, the use of a transmissive laser blocking filter at the radiation output 308 (as described above in respect of FIG. 1) is no longer necessary and transmission losses of the emitted radiation 322 are reduced or avoided. The corresponding increase in output power of the emitted radiation 322 represents a significant improvement.

Figure 1:
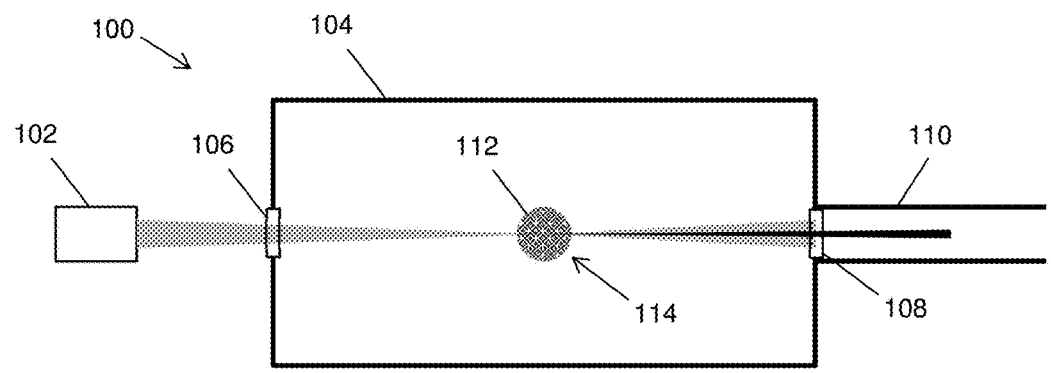
FIG. 1 is a schematic cross-sectional view of an apparatus for use as an HHG radiation source.

As in FIG. 1, the chamber 304 is configured to hold a vacuum, or at least to be nearly evacuated. The chamber 304 comprises a radiation input 306 that has a viewport the same or similar to that disclosed in respect of FIG. 1. The chamber 304 also comprises a radiation output 308, which includes an output plasma generator 316. The chamber 304 also includes an interaction region 314 at which a medium is present when in use. In the exemplary arrangement of FIG. 3, the medium is a gas 312, which may be one of the noble gases, such as argon.

The chamber is configured such that when driving radiation 320 emitted from a laser 302 propagates through the radiation input 306 and is incident on the medium 312, emitted radiation 322 is generated at the medium 312 by HHG. The emitted radiation 322 propagates through the radiation output 308 and the associated output plasma volume 318 and into the vacuum optical system 310, where it is manipulated and directed towards a wafer to be inspected. In the exemplary arrangement of FIG. 3, the output plasma generator 316 is configured to generate an output plasma volume 318 through which emitted radiation 322 can propagate.

Plasmas are gases in which a proportion of the atoms are ionized, resulting in free electrons. Plasmas have the property that their refractive index is dependent on the density of free electrons within the plasma. Because of this, a volume of plasma typically acts as a negative lens to a beam of radiation incident on and at least partially propagating through the volume of plasma, which typically defocuses the beam.

The output plasma generator 316 is configured to generate an output plasma volume that uses the plasma defocusing effect to at least partially filter out the driving radiation 320, such that the power of driving radiation 320 entering the output plasma volume 318 is greater than the power of the driving radiation 320 exiting the output plasma volume 318. This may be done by attenuation of the driving radiation 320 as it propagates through the output plasma volume 318 and/or by deflection of the driving radiation 320 as it propagates through the output plasma volume 318. It is noted that a proportion of the driving radiation 320 will be absorbed by the output plasma volume 318. Similarly, a proportion of the emitted radiation 322 will be absorbed by the output plasma volume 318. This absorption will be understood by the skilled person and it is noted that, in exemplary arrangements, the reduction in the power of the driving radiation 320 after passing through the output plasma volume 318 is greater than the reduction in power caused by such absorption. In some exemplary methods and apparatus, a ratio between the driving radiation 320 to the emitted radiation 322 after the output plasma volume 318 is reduced when compared to the same ratio before the output plasma volume 318.

In exemplary embodiments, the output plasma volume 318 may deflect a proportion of the driving radiation energy onto side walls of the output plasma generator 316. The sidewalls may then absorb at least part the deflected driving radiation 320, which is therefore substantially not reflected back into the output plasma generator 316. Driving radiation 320 that is deflected is prevented from exiting the output plasma volume 318 and entering the vacuum optical system 310 downstream of the chamber 304. The output plasma volume 318 is configured such that the emitted radiation 322 propagates through and is largely unaffected.

The output plasma generator 316 is configured to generate an output plasma volume that affects a property of the driving radiation 320 to a greater extent than the same property of the emitted radiation 322. In some exemplary embodiments, the property is a spatial profile of the beams of driving radiation 320 and emitted radiation 322. Spatial profile may encompass the shape of a beam and/or the size or divergence of a beam.

In some exemplary methods and apparatus, the driving radiation 320 may have a substantially lowest order Gaussian spatial profile before it is incident on the output plasma volume 318, meaning that the spatial profile of the driving radiation 320 has a lowest order Gaussian or lowest order Gaussian spatial profile. The output plasma volume 318 may be configured to deflect the beam of the driving radiation 320 radially outwards from an optical axis 324 of the output plasma volume 318.

In general, the density of free electrons in a plasma near the walls of a chamber confining the plasma is lower than the density of free electrons further away from the walls and nearer the centre of the chamber. Exemplary output plasma generators 316 may comprise a cylindrical channel for containing the output plasma volume 318. In such output plasma generators 316, there will be a higher free electron density on the optical axis 324 than near the cylindrical wall. Because the refractive index of a plasma is dependent on the free electron density, the refractive index in a plasma channel changes as function of radial position. This graded refractive index is such that the channel acts as a negative lens for a beam of driving radiation 320, defocusing it and deflecting the beam radially outwards from the optical axis 324. This effect is termed "plasma defocussing".

Figure 4:
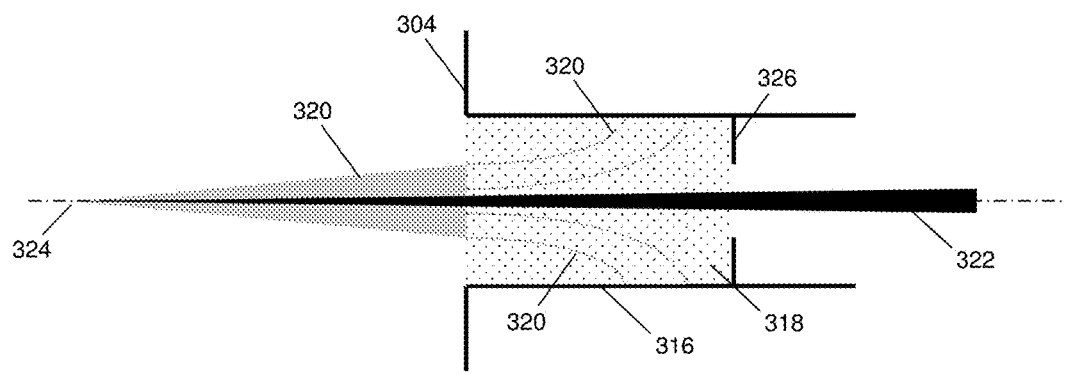
FIG. 4 is a schematic cross-sectional view of an output plasma generator of an apparatus for use as an HHG radiation source.

This is shown in FIG. 4, which shows a schematic cross-sectional view of the output plasma generator 316 and the output plasma volume 318. It can be seen from FIG. 4 that the driving radiation beam 320 diverges away from the optical axis 324 due to plasma defocussing. Exemplary chambers 304 may include an aperture 326 at a downstream end of the output plasma volume 318. The divergence of the driving radiation beam 320 means that deflected driving radiation 320 does not pass through the aperture 326 at the downstream end of the plasma output generator 316. As explained in greater detail below, the divergence of the emitted radiation beam 322 is lower than the divergence of the driving radiation beam 320 and in certain arrangements may be considered negligible.

Due to plasma defocusing, the intensity of the driving radiation beam 320, $I_{drive}$, on the optical axis 324 decreases as function of plasma length L as shown below.

$$I_{drive} = I_{drive0} \exp\left(-\frac{\eta n_a L^2}{2R^2 n_{cr}}\right) \quad (1)$$

where:

$I_{drive0}$ is the intensity of the driving radiation beam 320 incident on the output plasma volume 318;

$n_a$ is the atom density within the output plasma volume 318 on the optical axis 324;

$\eta$ is the proportion of atoms on the optical axis 324 that are ionized and R is the root mean square (rms) width of the Gaussian (or parabolic) output plasma volume 318 density profile; and $n_{cr}$ is the so-called critical electron density, which is a constant depending on the frequency of the driving radiation 320.

From equation (1), the output plasma volume length, L, needed to suppress the laser beam intensity on the optical axis to a fraction $F_1$ of the intensity incident, $I_{drive0}$, is given by:

$$L > \sqrt{\left(-\frac{2R^2 n_{cr} \ln F_1}{\eta n_a}\right)} \quad (2)$$

Based on equations (1) and (2), it can also be shown that the emitted radiation beam 322 that is emitted from the medium 312 by HHG is largely unaffected by plasma defocusing, and therefore passes through the aperture 326 undisturbed. This is because the refractive index contribution of the output plasma volume 318 due to free electrons is proportional to the wavelength of the radiation propagating through the output plasma volume 318 squared. Since the wavelengths of the emitted radiation are in a range from 1 nm to 100 nm and the driving radiation may be in a range from 0.8 μm to 1.2 μm, the plasma defocussing effect of the output plasma volume 318 is very much smaller for the emitted radiation beam 322. In some arrangements, the wavelengths of the emitted radiation are generally about 100 times shorter than that of the driving radiation 320 and the plasma defocusing effect on the emitted radiation beam 322 is therefore 10000 smaller compared to the effect on the driving radiation beam 320.

As set out above, the output plasma volume 318 may be used as a driving radiation 320 blocking filter. A limiting factor on this is use of plasma is that the atoms and ions comprising the output plasma volume 318 absorb part of the emitted radiation beam 322. Due to absorption, the intensity of the emitted radiation beam 322, $I_{emit}$, reduces as a function of output plasma volume 318 length, L, according to:

$$I_{emit} = I_{emit0} \exp(-\sigma(1-\eta) n_a L) \quad (3)$$

where:

$I_{emit0}$ is the intensity of the emitted radiation beam 322 incident on the output plasma volume 318;

$n_a$ is the atom density within the output plasma volume 318 on the optical axis 324; and $\sigma$ is the a cross section for absorption of the emitted radiation 322 by atoms, ions and/or molecules in the output plasma volume 318, which is a constant depending on the emitted radiation frequency and the atomic species of the output plasma volume 318.

From equation (3), an output plasma volume length 318 may be determined that does not absorb or attenuate the emitted radiation beam 322 by more than a fraction $F_2$ of the incident intensity, $I_{emit0}$.

$$L < -\frac{\ln F_2}{\sigma(1-\eta) n_a} \quad (4)$$

Therefore, the output plasma generator 316 may be configured to generate an output plasma volume 318 having a length, L, between that determined by equations (2) and (4). That is, in order to achieve sufficient driving radiation beam 320 diffraction and tolerable emitted radiation 322 absorption, the length conditions of equations (2) and (4) may be fulfilled simultaneously. Due to the fact that plasma defocusing scales quadratically with L (see equation (1)) and absorption scales only linearly with L (see equation (3)), there exists a density $n_a$ for which there is a range of L satisfying equations (2) and (4).

For example, taking an output plasma generator 316 configured to generate an output plasma volume 318 with hydrogen as the plasma species, an R=0.5 mm (which is typical in e.g. cascade arc plasmas), a driving radiation beam 320 with a 1 μm wavelength (which provides $n_{cr}$), an $n_a$ of $10^{23}$ m$^{-3}$, an ionization degree η=10% (also typical in e.g. cascade arc plasmas), and a desired driving radiation beam 320 attenuation of $F_1$=1%, equation (2) gives an output plasma volume length of >50 cm. With a desired emitted radiation beam 322 transmission of $F_2$=90%, equation (4) gives an output plasma volume 318 length, L, of at most 53 cm. This assumes emitted radiation 322 having a wavelength of 10 nm and a corresponding σ=2.2e$^{-24}$ m$^2$.

Therefore, L of 50 cm is able to both attenuate the driving radiation beam 320 by a factor 100 and transmit more than 90% of the emitted radiation beam 322. Such high emitted radiation 322 transmission is a considerable improvement over that of a zirconium filter (~50%) which is currently used.

As suggested by the equations above, significant reduction of the length of the output plasma volume 318 could be obtained by increasing the degree of ionization η of the output plasma volume 318. For example, η may be increased to more than 30%, more than 40%, more than 50%, more than 70% or more than 90%, the latter allowing for a output plasma volume 318 length of only a few centimeters. In order to achieve such ionization levels, the output plasma generator 316 may comprise a laser configured to ionize the output plasma volume 318.

As mentioned above, the output plasma volume 318 may be generated using hydrogen, although other gases may also be used.

In some arrangements, the output plasma volume 318 may be configured to transform the spatial profile of the beam of the driving radiation 320 from a substantially Gaussian spatial profile into a substantially annular spatial profile (an annular beam) in a plane transverse to the optical axis 324. In this context a substantially annular spatial profile is one that is annular or nearly annular in view of losses and errors in the system. The output plasma volume 318 might also deflect the beam radially outwards from the optical axis 324. An output plasma volume 318 with a Gaussian (or parabolic) radial electron density distribution away from the optical axis 324, and of sufficient density and length to satisfy equation 2 is able to transform the driving radiation beam 320 with a Gaussian spatial profile to a beam having an annular spatial profile.

Figure 5:
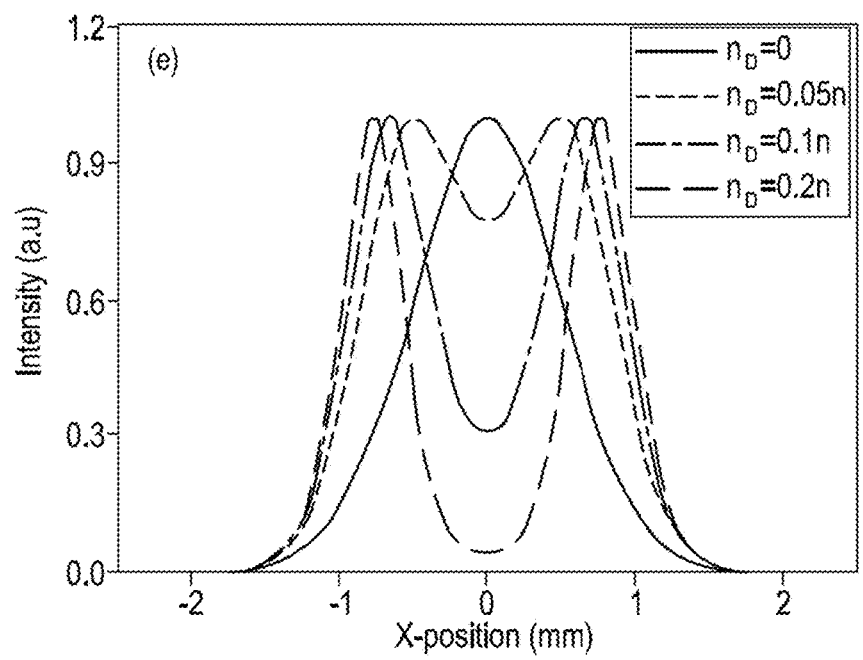
FIG. 5 is a plot of driving radiation beam intensities after travelling through plasma volumes having different atom densities.

FIG. 5 shows a plot of the intensity of the spatial profile of a driving radiation beam 320 after it has passed through output plasma volumes 318 having different ionizations. As can be seen, the intensity of the beam is altered to give different spatial profiles and, in the case where $n_a=0.2n_{cr}$, has been transformed into an annular beam. The emitted radiation beam 322 may be substantially spatially confined within the annular driving radiation beam 320, by which it is meant that a significant proportion, if not all, of the emitted radiation beam 322 is spatially confined within the peaks of intensity shown in FIG. 5 that define the annular beam of the driving radiation 320.

In such arrangements, the aperture 326, or iris, positioned at a downstream end of the output plasma generator 316, after the output plasma volume 318, is able to block the annularly spatially profiled driving radiation beam 320. The aperture 326 is sized to allow at least part of the emitted radiation 322 to pass through, while blocking at least part of the driving radiation 320. In certain exemplary arrangements, the aperture may be sized to block all or a majority of the driving radiation 320 and/or to allow all or a majority of the emitted radiation 322 to pass through.

It is noted here that the annular driving radiation beam 320 need not have zero or very low intensity at the centre (x=0 in FIG. 5), but need only have a reduced intensity at that point. The level of filtering provided by the output plasma volume 318 in combination with the aperture 326 may be proportional to the intensity of the driving radiation beam 320 at the centre.

Figure 6:
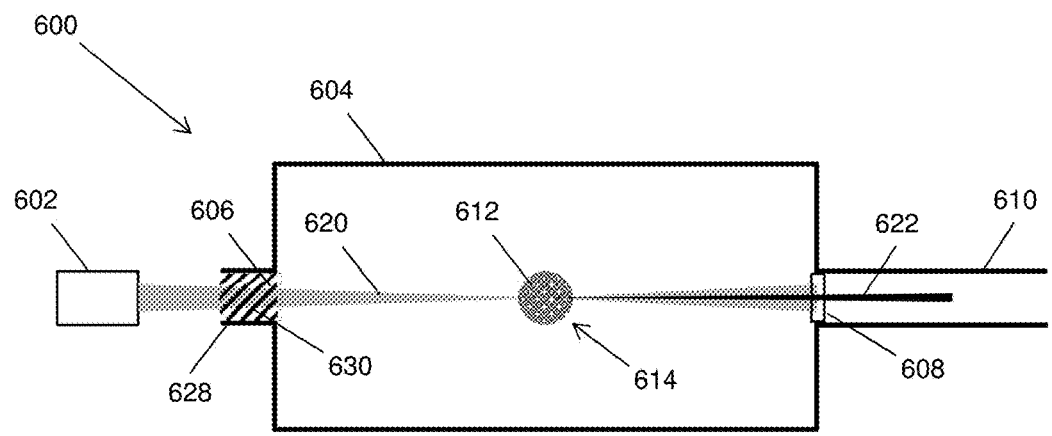
FIG. 6 is a schematic cross-sectional view of an apparatus for use as an HHG radiation source.

FIG. 6 shows a schematic representation of an alternative apparatus 600 for generation of radiation by HHG, which may be included in an inspection apparatus, such as the metrology apparatus 240. The apparatus 600 includes a number of features that are the same or similar to features shown in FIGS. 1 and 3, and such features may use the same reference numeral, prefixed with a "6" instead of a "1" or "3" respectively. In general, features of FIG. 6 are discussed insofar as they differ from those of FIGS. 1 and 3.

The apparatus 600 comprises an input plasma generator 628 at the radiation input 606. The input plasma generator 628 may replace the viewport described in FIGS. 1 and 3. The input plasma generator 628 is configured to generate an input plasma volume 630 through which driving radiation 620 may propagate. The input plasma volume 630 is configured to hold the vacuum in the chamber 604. That is, the input plasma volume 630 may form a barrier between two volumes of different pressures, for example an ambient air pressure outside of the chamber 604 and a vacuum or near vacuum in the chamber 604. The radiation output 608 is generally as described with reference to FIG. 1.

The input plasma generator 628 may comprise a generally cylindrical tube with open ends and is configured to generate the input plasma volume 630 within the cylindrical tube, such that it is filled with ionized gas. The input plasma generator 628 is configured to generate the input plasma volume 630 such that it can withstand a pressure difference between the ends of the tube, in some examples up to several hundred kPa. The input plasma volume 630 may also block the flow of gas from the high-pressure side to the low-pressure side. The input plasma volume 630 can therefore be used to separate the vacuum within the chamber 604 from atmosphere outside the chamber 604, without any use of viewports or other solid interfaces. In practical realizations of input plasma generators 628, the cylindrical tube has a diameter in a range from 4 mm to 6 mm and in one example 5 mm. However, wider diameters of cylindrical tube may be used, for example up to 20 mm, up to 30 mm or up to 50 mm. Further, the cylindrical tube may have a length in a range from 30 mm to 50 mm and in one example 40 mm.

Driving radiation 620 enters the chamber 604 by propagating through the input plasma volume 630. Therefore, there is no loss of power in the driving radiation 630 due to reflection, no limitation in light intensity that would otherwise damage solid viewports, and no beam degradation due to material defects.

The driving radiation 620 traverses the input plasma volume 630, which in general may lead to diffraction effects, due to the plasma defocusing effect described above. Because the refractive index of a plasma is dependent on the free electron density, the refractive index in the input plasma volume 630 changes as function of radial position. Typically, this graded refractive index is such that the channel acts as a negative lens for the driving radiation beam 620.

In exemplary arrangements, the input plasma generator 628 is configured to generate an input plasma 630 arranged such that the plasma defocusing effect is small and does not appreciably affect the driving radiation 620 and therefore does not appreciably affect the generation of emitted radiation 622 when the driving radiation 620 is incident on the medium 612.

Figure 7:
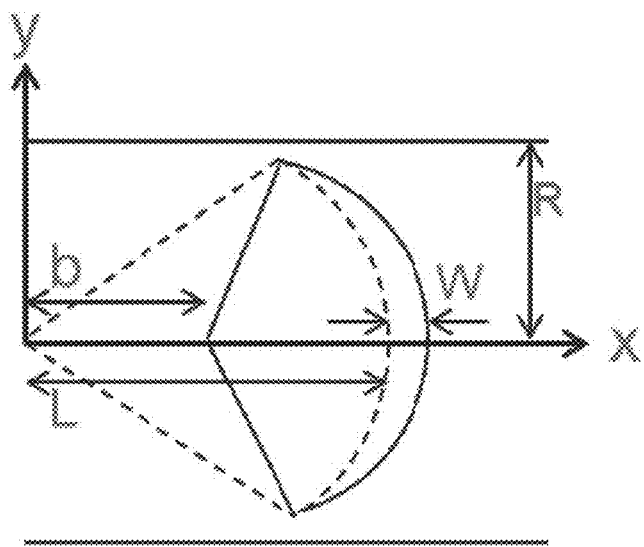
FIG. 7 is a diagram showing propagation of a wave-front.

FIG. 7 shows that the effect of plasma defocusing caused by the input plasma volume 630 on the driving radiation 620 can be considered negligible. In FIG. 7 a driving radiation beam is considered that is diverging from its focus at a point on the x-axis, x=0. At a downstream position, x=L, in a case where the beam has not propagated through a plasma volume, a wave-front of the beam would be part of a sphere with a centre at x=0, as indicated by the dashed curve. In a case where the beam propagates through a plasma volume, the plasma defocusing effect would lead to the wave-front being shifted forward on the x-axis by a distance W, as indicated by the solid curve. Consequently, the beam appears to have emanated from a shifted focal point at a position on the x-axis, x=b. As a criterion, one may consider plasma defocusing to have an insignificant effect on the driving radiation 620 and therefore on the generation of emitted radiation by HHG when b is smaller than the typical length scale of the laser focal region (called the Rayleigh range), which typically is a few mm. The Rayleigh range, $z_R$, is a common parameter used in laser optics when describing the focal region of a laser beam. For an ideal focused laser beam, the light intensity I varies as a function of distance z along an optical axis as $I \approx 1/[1+(z/z_R)^2]$. Therefore $z_R$ is approximately equal to the length of a high-intensity region relevant for HHG. Therefore, an apparent focal shift b insignificantly alters the HHG interaction as long as b is significantly smaller than $z_R$.

Therefore, in exemplary methods and apparatus, the input plasma generator 628 may be configured to generate an input plasma volume 630 having an electron density in a range from $10^{18}$ m$^{-3}$ to $10^{27}$ m$^{-3}$ and in a specific arrangement, $10^{23}$ m$^{-3}$, which is typical in a plasma volume. Further, the input plasma generator 628 may comprise a cylindrical tube for use as a plasma channel having a diameter of 5 mm and a length of 40 mm. In such a case, and assuming a plasma density of $10^{23}$ m$^{-3}$, the wave-front shift W may be calculated to be about 2 μm. The corresponding focus shift b may be calculated to be about 1 mm, which is smaller than the typical Rayleigh range used in a HHG source. In such arrangements, plasma defocusing would not have a significant effect on the driving radiation 620.

In other exemplary arrangements, the input plasma generator 628 is configured to generate an input plasma volume 630 configured such that the driving radiation beam 620 may be advantageously manipulated by the plasma defocusing effect of the input plasma volume 630. For example, the input plasma volume may be configured such that the defocusing effect is enlarged, which in general means that either the electron density or the plasma channel length are increased over those disclosed above. For example the input plasma volume may be generated such that $\eta=60\%$, $n_a=1e^{25}$ $m^{-3}$, L=10 cm, R=2.5 mm and F1=0.01, although such values of η may require laser ionization. As discussed above, an input plasma volume having sufficient electron density and/or length may transform a general lowest order Gaussian radiation beam into an annular shaped radiation beam. Therefore, the input plasma volume 630 may be configured to transform the driving radiation 620 into an annular beam.

Moreover, when the driving radiation beam 620 is transformed to an annular shaped beam and then focussed on the medium 612 by the input plasma volume 630, the driving radiation beam 620 leaves the medium (e.g. gas target) 612 of the apparatus 600 at different angles compared to the emitted radiation beam 622. That is, the annular beam has a broadly Gaussian profile at the focal point, at the medium 612 before diverging into an annular beam again downstream of the medium 612. In such arrangements, the driving radiation 620 can be blocked from entering the vacuum optical system 610 using an aperture at the radiation output 608, similar to that discussed above. This could obviate the need for a transmissive blocking filter at the radiation output 608 and avoid the corresponding transmission loss of emitted radiation power.

Figure 8:
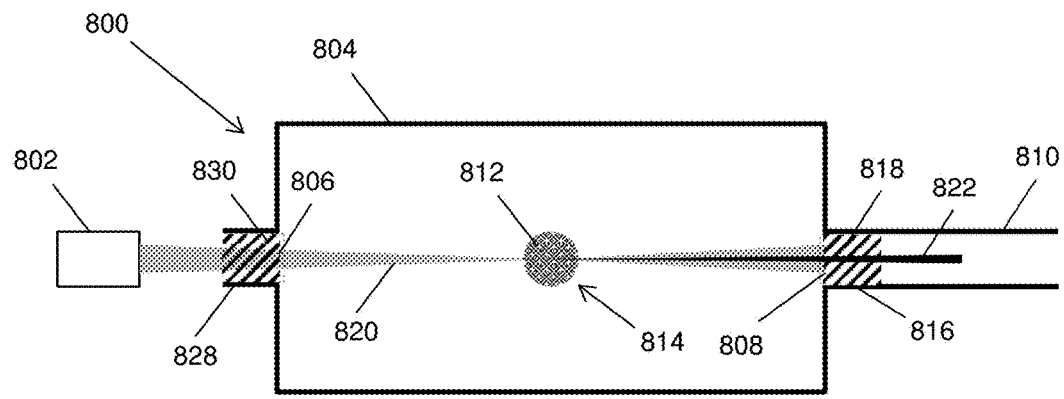
FIG. 8 is a schematic cross-sectional view of an apparatus for use as an HHG radiation source.

FIG. 8 shows a schematic representation of an alternative apparatus 800 for generation of radiation by HHG, which may be included in an inspection apparatus, such as the metrology apparatus 240. The apparatus 800 includes a number of features that are the same or similar to features shown in FIGS. 1, 3 and 6, and such features may use the same reference numeral, prefixed with a "8" instead of a "1", "3" or "6" respectively. In general, features of FIG. 8 are discussed insofar as they differ from those of FIGS. 1, 3 and 6. Exemplary apparatus 800 comprises an output plasma generator 816 according to any described herein and an input plasma generator 828 according to any described herein.

Figure 9:
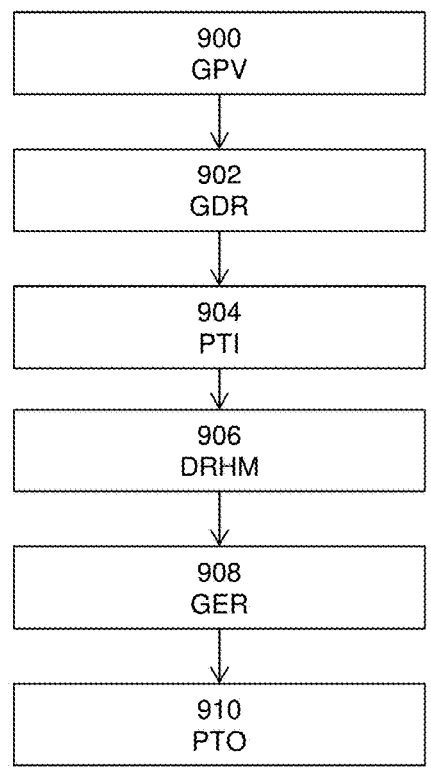
FIG. 9 is a flow diagram showing a method for generating radiation by HHG using one of the apparatus disclosed herein.

FIG. 9 shows a method for generating radiation by high harmonic generation, HHG, using any apparatus described herein, and in particular in FIGS. 3, 6 and 8.

The method comprises generating 900, GPV, by at least one plasma generator located at one or both of the radiation input or the radiation output of the chamber, a plasma volume. In accordance with FIGS. 3, 6 and 8, exemplary apparatus may comprise an output plasma generator 316, 816 and/or an input plasma generator 628, 828 and generating the plasma volume may therefore comprises generating an output plasma volume 318, 818 and/or an input plasma volume 630, 830. For the remainder of the description of FIG. 9, FIG. 3 is referred to and it is assumed that an output plasma volume 318 is generated, but it will be appreciated that an input plasma volume 630, 830 may alternatively or additionally be generated.

Driving radiation 320 is generated 902, GDR, by, for example, the laser 302. The driving radiation 320 may have a wavelength in a range from 0.8 μm to 1.2 μm and may, in a specific example have a wavelength of 1 μm. The driving radiation 320 is emitted towards the radiation input 306 of the chamber 304 and propagates 904, PTI, therethrough. In the case of FIG. 3, the radiation input 306 comprises a viewport, as described herein.

The driving radiation 320 is incident 906, DRHM (Driving Radiation Hits Medium), on the medium 312, which may be a gas target, as described herein. Emitted radiation 322 is therefore generated 908, GER, by HHG. The emitted radiation 322 may comprise radiation at wavelengths in ranges from 1 nm to 10 nm, from 5 nm to 50 nm or from 1 nm to 100 nm.

According to any of the means discussed above, the emitted radiation 322 propagates 910, PTO, through the output plasma volume 318 and at least part of the driving radiation 320 is attenuated, deflected or otherwise prevented from propagating through the output plasma volume 318.

Referring to FIG. 6, the apparatus 600 may comprise an input plasma generator 628 and generating the plasma volume 900 may comprise generating the input plasma volume 630. In such methods, propagation 904 of the driving radiation 620 through the radiation input 606 may comprise propagation through the input plasma volume 630. After generation 908 of the emitted radiation 622, the driving radiation 620 and the emitted radiation 622 may propagate through a transmissive laser blocking filter, as described above.

Referring to FIG. 8, the apparatus 800 comprises an input plasma generator 828 and an output plasma generator 816. Therefore, generating the plasma volume 900 may comprise generating the input plasma volume 830 and the output plasma volume 818. In such methods, propagation 904 of the driving radiation 820 through the radiation input 806 may comprise propagation through the input plasma volume 830. After generation 908 of the emitted radiation 822, the driving radiation 820 and the emitted radiation 822 may propagate through the output plasma volume 818, as described above.

Figure 10:
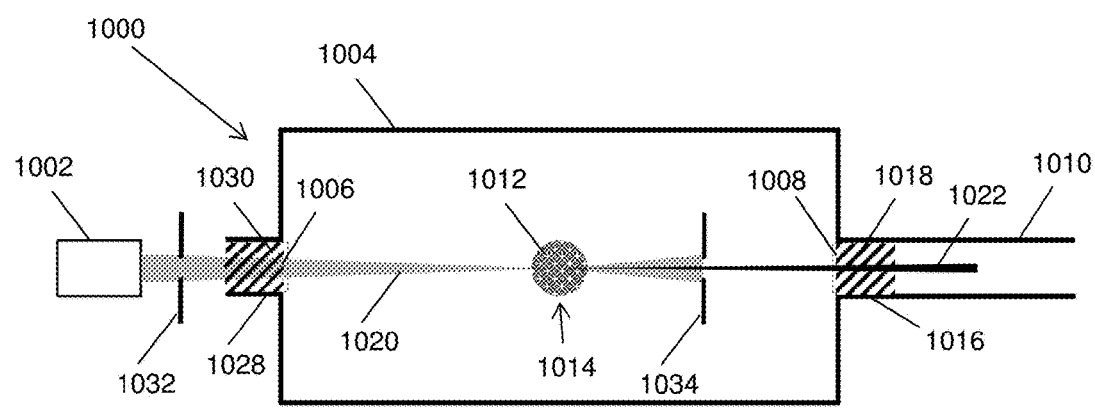
FIG. 10 is a schematic cross-sectional view of an apparatus for use as an HHG radiation source.

FIG. 10 shows a further exemplary apparatus 1000. As with other apparatus disclosed herein, the apparatus 1000 comprises a number of features that are the same or similar to those already described herein. Such features are not described in detail again here. The apparatus 1000 comprises a first, or entrance, aperture, which may be an entrance iris 1032. The entrance iris has a diameter of aperture configured to cause diffraction of the driving radiation 1020. The diffraction of the driving radiation may be such that after passing through an aperture of the entrance iris 1032, the driving radiation will propagate in such a way as to create one or more positions at which the driving radiation has an intensity minimum and/or has an annular or substantially annular spatial profile. That is, a section through the driving radiation 1020 transverse the direction of propagation will show a substantially annular distribution of the driving radiation 1020. In this context, a substantially annular spatial profile is as defined above.

A second, or exit, aperture, which may be an exit iris 1034 may be positioned after the gas target 1012 and at a point in the propagation of the driving radiation 1020 at which an intensity minimum and/or substantially annular spatial profile is exhibited. The aperture of the exit iris 1034 may be configured to block at least part of the driving radiation and may be based on the annular spatial profile thereof. In exemplary arrangements, the exit iris 1034 may be configured to block more than 50%, more than 60%, more than 70%, more than 80% or more than 90% of the driving radiation 1020.

Referring to FIG. 10 in more detail, the entrance iris 1032 is positioned upstream of the radiation input 1006, between the laser 1002 and the radiation input 1006 of the chamber 1004. Further, the exit iris 1034 is positioned downstream of the interaction region 1014 and, in the specific example of FIG. 10, between the interaction region 1014 and the radiation output 1008 of the chamber 1004. However, it is noted that the entrance iris and the exit iris may each be differently positioned and still achieve the same result as the apparatus 1000 shown in FIG. 10. For example, the entrance iris 1032 may be positioned in the chamber 1004, downstream of the radiation input 1006. The entrance iris 1032 may be positioned between the radiation input 1006 and the interaction region 1014.

The driving radiation 1020 passes through the entrance iris 1032 before it enters the chamber 1004. The entrance iris 1032 has an advantageously chosen diameter configured to diffract the driving radiation 1020 as it passes therethrough. Due to diffraction effects caused by the entrance iris 1032, there exist a number of positions along the propagation path of the driving radiation 1020 at which the driving radiation beam has an annular profile. In particular, such positions will be present also downstream of the interaction region 1014. This property of diffraction is utilised by placing the second, exit iris 1034 at a position downstream of the interaction region 1014. The exit iris 1034 is located at a position where the driving radiation beam has a substantially annular spatial profile. A diameter of an aperture in the exit iris 1034 is configured to block at least part of the driving radiation 1020, as explained above. In an exemplary arrangement, the aperture in the exit iris 1034 may be smaller than a central hole in the annular spatial profile of the driving radiation. Consequently, all or a substantial fraction of the laser light in the driving radiation 1020 will be blocked by the exit iris 1034. The driving radiation 1020 is thereby prevented from entering the sensitive vacuum (SXR) optical system.

The emitted radiation 1022, which may be an SXR beam, that is emitted by the gas target 1012 is directed along the optical axis of the driving radiation 1020, but has a substantially lower divergence than the driving radiation 1020. Therefore the emitted radiation 1022 is able to pass through the hole of the exit iris 1034 unaffected. The emitted radiation 1022 and driving radiation 1020 are effectively separated by the exit iris 1034, which may effectively replace the function of the zirconium filter. In other exemplary arrangements, the entrance iris 1032 and exit iris 1034 may be used in combination with a zirconium filter at the radiation output 1008, the zirconium filter being used to further filter out the (reduced) amount of driving radiation 1020 that passes through the exit iris 1034.

Figure 11:
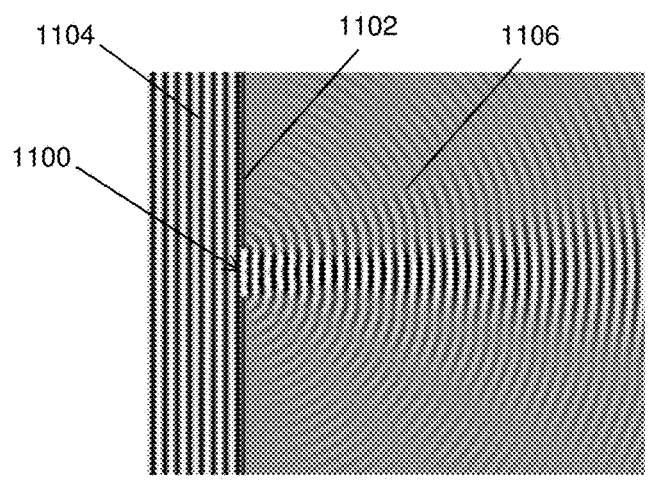
FIG. 11 is a representation of diffraction of a radiation beam passing through an aperture.

FIG. 11 shows a representation of a physical effect that is made use of in the exemplary apparatus of FIG. 10, namely the diffraction of a beam of laser light by the edges of a circular aperture 1100 in an iris 1102, such as the entrance iris 1032. The laser light 1104 passes through the aperture 1100 to produce diffracted laser light 1106. Diffraction is due to the wave character of light, and the interaction of the light wave with the hard edges of the aperture 1100 in general causes a pattern of intensity maxima and intensity minima downstream of the aperture 1100. FIG. 11 illustrates one example of such diffraction, where radial lines of high and low light intensity are visible. As used herein, an intensity maximum encompasses a point along the propagation path of the driving radiation 1020 at which the intensity of the driving radiation 1020 reaches a peak. An intensity maximum does not have to be the highest intensity of the driving radiation 1020 taking account of the complete propagation path and there may therefore be a plurality of maxima. For similar reasons, there may also be a plurality of intensity minima.

Figure 12:
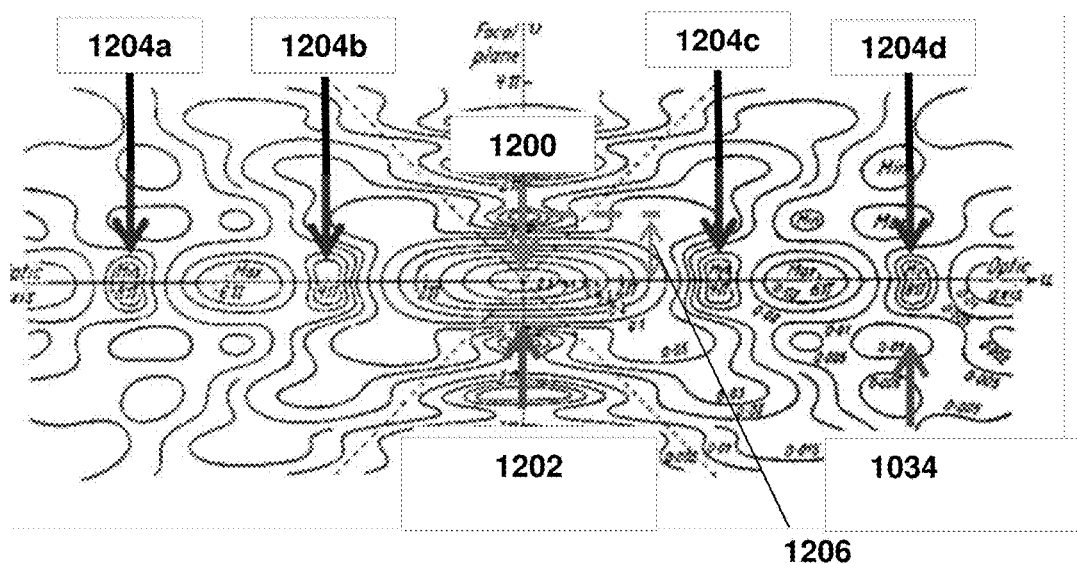
FIG. 12 is a representation of an intensity pattern of radiation beam after passing through an aperture.

In the exemplary apparatus of FIG. 10, the driving radiation 1020 passing through the entrance iris 1032 may comprise a laser beam that is focused onto the gas target 1012. In this case, a complicated intensity pattern results in a region near the focus. FIG. 12 shows this pattern as can be analytically derived, for example in Born and Wolf, Principles of Optics (1986). The contour lines show lines of equal intensity of the driving radiation 1020. The geometric focus is indicated by the arrow 1200 and the position of the gas target 1012 is shown by the arrow 1202 to be at or near the point of geometric focus 1200. Locations with minimal or zero intensity on the optical axis (i.e. an annular spatial profile) are indicated by arrows 1204a-d. From FIG. 12, it is seen that the intensity pattern in a plane perpendicular to the optical axis (the horizontal axis in FIG. 12) at one of the locations 1204a-d exhibits a hole at the center. That is, the driving radiation 1020 is essentially annular at those positions. In exemplary arrangements, the exit iris 1034 may be positioned at one of the locations 1204a-d, e.g. the position 1204c or 1204d indicated in FIG. 12.

In exemplary apparatus 1000, the location of the exit iris 1034 is positioned at a distance from the geometric focus 1200 in order to avoid excessive laser intensity on the iris material that could cause damage. The intensity minima 1204a-d on the optical axis may, in principle, repeat indefinitely. In particular arrangements, the intensity minima 1204a-d are located at distances $z_N$ from the geometric focus 1200, which may be given by:

$$z_N = 8N\lambda(f/\#)^2$$

where N is an integer, $\lambda$ is the wavelength of the driving radiation 1020 and f/# is the so-called f-number of the optical system which is equal to the distance from the entrance iris 1032 to the geometric focus 1200 divided by the diameter of the entrance iris 1032. Typical values include one or more of a wavelength of 1 μm and an f-number of 20, giving an intensity minimum 1204a-d approximately every 3 mm.

In order to estimate which of the intensity minima 1204a-d is sufficiently far from the geometric focus 1200 so as to avoid damage of the exit iris 1034 material, the ablation threshold may be used for metals with laser pulses with a length of approximately tens of femtoseconds, which is typical for HHG applications. This threshold may be approximately 0.5 J/cm$^2$ per laser pulse. Considering exemplary driving radiation 1020 having a laser pulse with a length of 30 fs (full width at half maximum), a peak intensity of about 10$^{17}$ W/m$^2$ may be determined. This is about 3% of the intensity at the geometric focus 1200 that is typically applied at an HHG gas target 1012, which may be about 3×10$^{18}$ W/m$^2$. The requirement to avoid iris damage may therefore be achieved when the intensity of the driving radiation 1020 at the plane 1204d where the exit iris 1034 is placed does not exceed about 3% of the intensity of the driving radiation 1020 at the geometric focus 1200. In other arrangements, the intensity of the driving radiation 1020 at the plane 1204d where the exit iris 1034 is placed may be less than about 15%, 10% or 5% of the intensity of the driving radiation 1020 at the geometric focus 1200.

From the intensity map of FIG. 12, it can be seen that this condition is approximately met for all intensity minima

1204a-1024d. Given the estimate above for the locations of the intensity minima 1204a-d, exemplary apparatus may include an exit iris 1034 at a distance from the geometric focus 1200 in a range from about 0.1 mm to 10 mm, in a range from about 2 mm to 4 mm, or of about 3 mm. In other exemplary apparatus, an optical system may use high-NA (numerical aperture) optics, for which the f-number can be as low as f/#~1. For such exemplary apparatus, the exit iris 1034 position may be at approximately 8 µm from the focus 1200. In principle the exit iris 1034 may be at any number of possible distances from the focus 1200 since the intensity minima 1204a-1024d continue indefinitely (i.e. an arbitrarily large N).

In further exemplary apparatus, the transverse size of the intensity minima 1204a-d (i.e. the internal diameter or the diameter of the 'hole' in the annular spatial profile) should be sufficiently large to allow the emitted radiation beam 1022, which is emitted by the gas target 1012 located at or near the geometric focus 1200, to pass through. In exemplary apparatus, the entrance iris 1032 is configured such that the transverse diameter of the emitted radiation beam 1022 at the geometric focus 1200 is in a range from 5 µm to 15 µm and in some arrangements may be about 10 µm or less. In exemplary apparatus, the entrance iris 1032 is configured such that the transverse diameter of the emitted radiation beam 1022 diverges at an angle in a range from 3 mrad to 5 mrad and, in a specific example may be about 4 mrad, downstream of the geometric focus 1200. Therefore, the approximate diameter of the emitted radiation beam 1022 at a distance of approximately 3 mm downstream from the geometric focus (i.e. at a possible position for the exit iris 1032) is approximately 23 µm.

In other exemplary apparatus, the aperture diameter of the exit iris 1034 should be at most the internal diameter of the annular spatial profile of the driving radiation 1020 at the intensity minimum 1204d at which the exit iris 1034 is positioned. It is noted that the internal diameter of the annular spatial profile of the driving radiation 1020 at the intensity minimum 1204d may be approximately equal to a well-known distance in the focal plane indicated by the arrow 1206. This distance is equal to $1.22\lambda(f/\#)$. Accordingly, in exemplary arrangements, the aperture diameter of the exit iris 1034 may be determined using the same formula and may be in a range from 20 µm to 30 µm and in a specific example may be approximately 24 µm. It is also noted that this aperture diameter of the exit iris 1034 is somewhat larger than the estimated size of the emitted radiation beam 1022 and the exit iris 1034 is small enough to block the majority of driving radiation 1020 yet large enough to allow the emitted radiation beam 1022 to pass unhindered.

The exemplary apparatus 1000 of FIG. 10 includes an input plasma volume 1030 and an output plasma volume 1018. However, it will be understood that the entrance and exit irises 1032, 1034 may be used with apparatus in which one or both of the input plasma volume 1030 and the output plasma volume 1018 is not present, in which case they may be replaced by the corresponding features of FIG. 1.

A computer program may be configured to provide any of the above described methods. The computer program may be provided on a computer readable medium. The computer program may be a computer program product. The product may comprise a non-transitory computer usable storage medium. The computer program product may have computer-readable program code embodied in the medium configured to perform the method. The computer program product may be configured to cause at least one processor to control an apparatus to perform some or all of the method.

Various methods and apparatus are described herein with reference to block diagrams or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

Computer program instructions may also be stored in a computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-ray).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus control an apparatus to provide steps for implementing the functions/acts specified in the block diagrams and/or flowchart block or blocks.

Accordingly, the invention may be embodied in hardware and/or in software (including firmware, resident software, micro-code, etc.) that runs on a processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated.

Further embodiment are defined in the subsequent numbered clauses:

1. An apparatus for generation of radiation by high harmonic generation, HHG, the apparatus comprising:

a chamber for holding a vacuum, the chamber comprising a radiation input, a radiation output and an interaction region at which, in use, a medium is present, the chamber being arranged such that, in use, when driving radiation propagates through the radiation input and is incident upon the medium, the medium emits radiation via HHG, the emitted radiation propagating through the radiation output; and at least one plasma generator at the radiation input and/or the radiation output for generating a plasma volume allowing the driving radiation and emitted radiation, respectively, to propagate through the plasma volume.

2. The apparatus according to clause 1, wherein the at least one plasma generator is an output plasma generator at the radiation output and is configured to generate an output plasma volume for filtering the driving radiation such that less driving radiation exits the output plasma volume than enters the output plasma volume.

3. The apparatus according to clause 2, wherein the output plasma generator is configured to generate the output plasma volume for altering one or more properties of the driving radiation to a greater degree than the same one or more properties of the emitted radiation.

4. The apparatus according to clause 3, wherein the one or more properties comprise a spatial profile of the driving and emitted radiation.

5. The apparatus according to any of clauses 2 to 4, wherein the output plasma generator is configured to generate the output plasma volume for transforming the driving radiation from a substantially lowest order Gaussian spatial profile to a substantially annular spatial profile.

6. The apparatus according to any preceding clause, wherein the chamber further comprises an aperture at the radiation output sized to block at least part of the driving radiation and to allow the emitted radiation to pass through.

7. The apparatus according to clause 5 or 6, wherein at least part of the emitted radiation is substantially spatially confined within the annular spatial profile of the driving radiation.

8. The apparatus according to any of clauses 2 to 7, wherein the output plasma generator is configured to generate the output plasma volume for deflecting the driving radiation radially away from an output optical axis of the apparatus.

9. The apparatus according to any of clauses 2 to 8, wherein the output plasma generator comprises a cylindrical channel, and is configured to generate the output plasma volume with a density of free electrons decreasing radially from an output optical axis through the cylindrical channel.

10. The apparatus according to clause 9, wherein the decrease in the density of free electrons in the output plasma volume has a parabolic function.

11. The apparatus according to clause 10, wherein the output plasma generator is configured to generate the output plasma volume having a length, $L$, in a range determined by $$L > \sqrt{-\frac{2R^2 n_{cr} \ln F_1}{\eta n_a}}$$

and $$L < -\frac{\ln F_2}{\sigma(1-\eta)n_a}$$

where $\eta$ is a degree of ionization within the plasma, $n_a$ is an ionized atom density on the output optical axis, $R$ is the root mean square width of the Gaussian function, $n_{cr}$ is the critical electron density, $\sigma$ is a cross section for absorption of the emitted radiation by atoms, ions and/or molecules in the output plasma volume, $F_1$ is an attenuation factor of the driving radiation and $F_2$ is an attenuation factor of the emitted radiation.

12. The apparatus according to any of clauses 2 to 11, wherein the output plasma generator is configured to generate the output plasma volume as an arc plasma and optionally a cascaded arc plasma comprising a noble gas or hydrogen.

13. The apparatus according to any of clauses 2 to 12, wherein the output plasma generator is configured to generate the output plasma volume using laser ionization and optionally having a degree of ionization of greater than 50%.

14. The apparatus according to any preceding clause, wherein the at least one plasma generator comprises an input plasma generator at the radiation input and is configured to generate an input plasma volume for holding the vacuum in the chamber.

15. The apparatus according to clause 14, wherein the input plasma generator is configured to generate the input plasma volume using one of the noble gases.

16. The apparatus according to clause 15, wherein the noble gas is argon.

17. The apparatus according to any of clauses 14 to 16, wherein the input plasma generator is configured to generate the input plasma volume for transforming the driving radiation from a substantially lowest order Gaussian spatial profile to a substantially annular spatial profile.

18. The apparatus according to any of clauses 14 to 17, wherein the input plasma generator is configured to generate the input plasma volume for focussing the driving radiation at the interaction region.

19. The apparatus according to any of clauses 14 to 18, wherein the input plasma generator comprises a cylindrical channel, and is configured to generate the input plasma volume having a density of free electrons decreasing radially from an input optical axis through the cylindrical channel.

20. The apparatus according to any of clauses 14 to 19, wherein a length of the input plasma volume is in a range from 30 mm to 100 mm and/or wherein a diameter of the input plasma volume is in a range from 3 mm to 55 mm.

21. The apparatus according to any preceding clause, wherein the driving radiation has a wavelength in a range from 0.8 μm to 1.2 μm and/or wherein the emitted radiation comprises radiation at multiple wavelengths in a range from 1 nm to 100 nm.

22. The apparatus according to any preceding clause, wherein the interaction region comprises a chamber configured to hold a gas.

23. The apparatus according to clause 22, wherein the gas is one of a noble gas, nitrogen, oxygen and air.

24. An inspection apparatus comprising the apparatus of any of clauses 1 to 23, and further comprising a substrate table for holding a substrate and optics for directing the emitted radiation onto the substrate.

25. The inspection apparatus of clause 24, wherein the inspection apparatus is a metrology apparatus.

26. A method for generating radiation by high harmonic generation, HHG, using an apparatus comprising:
 a chamber comprising a radiation input, a radiation output and an interaction region at which, in use, a medium is present; and
 at least one plasma generator at the radiation input and/or the radiation output,
 the method comprising:
 generating, by the at least one plasma generator, a plasma volume at the radiation input and/or a plasma volume at the radiation output; and
 propagating driving radiation through the radiation input such that the driving radiation is incident upon the medium, causing the medium to emit radiation via HHG, the emitted radiation propagating through the radiation output,
 wherein the plasma volume at the radiation input allows the driving radiation to propagate through, and the plasma volume at the radiation output allows the emitted radiation to propagate through.

27. A computer program comprising instructions which, when executed on at least one processor, cause the at least one processor to control an apparatus to carry out the method according to clause 26.

28. A carrier containing the computer program of clause 27, wherein the carrier is one of an electronic signal, optical signal, radio signal, or non-transitory computer readable storage medium.

29. The apparatus according to any one of the clauses 1 to 23, further comprising an entrance aperture upstream of the interaction region and configured to diffract the driving radiation as it passes therethrough such that a plurality of intensity minima are produced in the driving radiation downstream of the entrance aperture.

30. The apparatus according to clause 29, wherein the entrance aperture is configured to diffract the driving radiation such that the driving radiation has a substantially annular spatial profile at one or more of the intensity minima.

31. The apparatus according to clause 30, wherein the entrance aperture is configured such that an internal diameter of one or more of the plurality of intensity minima is sufficient to allow the emitted radiation to pass through.

32. The apparatus according to any of clauses 29 to 31, wherein the entrance aperture is positioned upstream of the radiation input.

33. The apparatus according to any of clauses 29 to 32, further comprising an exit aperture positioned at one of the plurality of intensity minima and configured to block at least part of the driving radiation.

34. The apparatus according to clause 33, wherein the exit aperture is positioned downstream of the interaction region.

35. The apparatus according to claim 33 or 34 when dependent directly or indirectly on claim 30, wherein a diameter of the exit aperture is less than or equal to an internal diameter of the substantially annular spatial profile of the driving radiation.

36. The apparatus according to clause 35, wherein the diameter of the exit aperture is greater than or equal to a distance determined by 1.22λ(f/#), wherein λ is the wavelength of the driving radiation and f# is the f-number corresponding to a relationship between the entrance aperture and a geometric focus of the driving radiation.

37. The apparatus according to any of clauses 32 to 36, wherein the exit aperture is positioned at an intensity minimum at which the intensity of the driving radiation is less than 15% of the intensity of the driving radiation at the interaction region.

38. The apparatus according to any of clauses 32 to 37, wherein the exit aperture is positioned in a range from 0.5 cm to 1.5 cm from a center of the interaction region.

The skilled person will be able to envisage other embodiments without departing from the scope of the appended claims.

Although specific reference may be made in this text to the use of lithographic apparatus in the manufacture of ICs, it should be understood that the lithographic apparatus described herein may have other applications. Possible other applications include the manufacture of integrated optical systems, guidance and detection patterns for magnetic domain memories, flat-panel displays, liquid-crystal displays (LCDs), thin-film magnetic heads, etc.

Although specific reference may be made in this text to embodiments of the invention in the context of a metrology apparatus, embodiments of the invention may be used in other apparatus. Embodiments of the invention may form part of a mask inspection apparatus, a lithographic apparatus, or any apparatus that measures or processes an object such as a wafer (or other substrate) or mask (or other patterning device). These apparatus may be generally referred to as lithographic tools. Such a lithographic tool may use vacuum conditions or ambient (non-vacuum) conditions.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the claims set out below.

The invention claimed is:

1. An apparatus for generation of radiation by high harmonic generation (HHG) the apparatus comprising:
 a chamber for holding a vacuum, the chamber comprising a radiation input, a radiation output and an interaction region at which, wherein the chamber is configured to contain a medium and arranged to receive a driving radiation that propagates through the radiation input so as to be incident upon the medium to emit radiation by HHG, the emitted radiation propagating through the radiation output; and
 at least one plasma generator at the radiation input and/or the radiation output for generating a plasma volume allowing the driving radiation and emitted radiation, respectively, to propagate through the plasma volume.

2. The apparatus of claim 1, wherein the at least one plasma generator is an output plasma generator located at the radiation output and is configured to generate an output plasma volume for filtering the driving radiation such that less driving radiation exits the output plasma volume than enters the output plasma volume.

3. The apparatus of claim 2, wherein the output plasma generator is configured to generate the output plasma volume for altering one or more properties of the driving radiation and wherein the one or more properties comprise a spatial profile of the driving and emitted radiation.

4. The apparatus of claim 2, wherein the output plasma generator is configured to generate the output plasma volume for transforming the driving radiation from a substantially lowest order Gaussian spatial profile to a substantially annular spatial profile.

5. The apparatus of claim 4, wherein at least part of the emitted radiation is substantially spatially confined within the annular spatial profile of the driving radiation.

6. The apparatus of claim 2, wherein the output plasma generator is configured to generate the output plasma volume for deflecting the driving radiation radially away from an output optical axis of the apparatus.

7. The apparatus of claim 2, wherein the output plasma generator comprises a cylindrical channel, and the output plasma generator is configured to generate the output plasma volume with a density of free electrons decreasing radially from an output optical axis through the cylindrical channel.

8. The apparatus of claim 7, wherein the decrease in the density of free electrons in the output plasma volume has a parabolic function, and wherein the output plasma generator is configured to generate the output plasma volume having a length, L, in a range determined by $$L > \sqrt{-\frac{2R^2 n_{cr} \ln F_1}{\eta n_a}}$$

and $$L < -\frac{\ln F_2}{\sigma(1-\eta) n_a}$$

where $\eta$ is a degree of ionization within the plasma, $n_a$ is an ionized atom density on the output optical axis, R is the root mean square width of the Gaussian function, $n_{cr}$ is the critical electron density, $\sigma$ is a cross section for absorption of the emitted radiation by atoms, ions and/or molecules in the output plasma volume, $F_1$ is an attenuation factor of the driving radiation and $F_2$ is an attenuation factor of the emitted radiation.

9. The apparatus of claim 2, wherein the output plasma generator is configured to generate the output plasma volume using laser ionization and optionally having a degree of ionization of greater than 50%.

10. The apparatus of claim 1, wherein the chamber further comprises an aperture at the radiation output sized to block at least part of the driving radiation and to allow the emitted radiation to pass through.

11. The apparatus of claim 1, wherein the at least one plasma generator comprises an input plasma generator at the radiation input and is configured to generate an input plasma volume for holding the vacuum in the chamber and, wherein the input plasma generator is configured to generate the input plasma volume for transforming the driving radiation from a substantially lowest order Gaussian spatial profile to a substantially annular spatial profile.

12. The apparatus of claim 11, wherein the input plasma generator is configured to generate the input plasma volume for focusing the driving radiation at the interaction region.

13. The apparatus of claim 1, further comprising an entrance aperture upstream of the interaction region and configured to diffract the driving radiation as it passes therethrough such that a plurality of intensity minima are produced in the driving radiation downstream of the entrance aperture.

14. The apparatus of claim 13, wherein the entrance aperture is configured to diffract the driving radiation such that the driving radiation has a substantially annular spatial profile at one or more of the plurality of intensity minima.

15. The apparatus of claim 14, wherein the entrance aperture is configured such that an internal diameter of one or more of the plurality of intensity minima is sufficient to allow the emitted radiation to pass through.

16. The apparatus of claim 13, wherein the entrance aperture is positioned upstream of the radiation input.

17. The apparatus of claim 13, further comprising an exit aperture positioned at one of the plurality of intensity minima and configured to block at least part of the driving radiation.

18. The inspection apparatus comprising the apparatus of claim 1, and further comprising a substrate table for holding a substrate and optics for directing the emitted radiation onto the substrate and wherein, optionally, the inspection apparatus is a metrology apparatus.

19. A method for generating radiation by high harmonic generation (HHG), comprising:
  containing a medium in an interaction region of a chamber, wherein the chamber comprises a radiation input and a radiation output; and
  generating a plasma at the radiation input and/or the radiation output with at least one plasma generator,
  generating, by the at least one plasma generator, a plasma volume at the radiation input and/or a plasma volume at the radiation output; and
  propagating driving radiation through the radiation input such that the driving radiation is incident upon the medium, causing the medium to emit radiation by HHG, the emitted radiation propagating through the radiation output,
  wherein the plasma volume at the radiation input allows the driving radiation to propagate through, and the plasma volume at the radiation output allows the emitted radiation to propagate through.

20. A computer program comprising instructions that, when executed on at least one processor, cause the at least one processor to control an apparatus to carry out the method according to claim 19.

* * * * *